United States Patent
Flagan et al.

[11] Patent Number: 6,003,389
[45] Date of Patent: Dec. 21, 1999

[54] ENHANCED AUTOMATED CLASSIFIED AEROSOL DETECTOR

[75] Inventors: Richard C. Flagan, La Canada; Donald R. Collins, Pasadena, both of Calif.

[73] Assignee: California Institute of Technology, Pasadena, Calif.

[21] Appl. No.: 08/924,372

[22] Filed: Sep. 5, 1997

Related U.S. Application Data

[60] Provisional application No. 60/025,835, Sep. 5, 1996.

[51] Int. Cl.$^6$ .......................... G01N 15/00; G01N 27/62
[52] U.S. Cl. ........................................... 73/865.5; 324/464
[58] Field of Search ................................ 73/865.5, 28.01, 73/28.02, 28.04, 863.21; 324/452, 464

[56] References Cited

U.S. PATENT DOCUMENTS

| | | | |
|---|---|---|---|
| 3,763,428 | 10/1973 | Preist | 73/28.01 |
| 4,556,849 | 12/1985 | Kalakutsky et al. | 324/464 |
| 4,769,609 | 9/1988 | Masuda | 73/865.5 |
| 4,790,650 | 12/1988 | Keady | 73/28.01 |
| 5,117,190 | 5/1992 | Pourprix | 324/452 |
| 5,150,036 | 9/1992 | Pourprix | 73/28.02 |
| 5,150,037 | 9/1992 | Kouzuki | 73/865.5 |
| 5,571,945 | 11/1996 | Koutrakis et al. | 73/28.03 |
| 5,596,136 | 1/1997 | Flagan et al. | 73/28.04 |
| 5,606,112 | 2/1997 | Flagan et al. | 73/28.04 |
| 5,777,245 | 7/1998 | Chandrachood et al. | 73/865.5 |

OTHER PUBLICATIONS

A. Bucholski and R. Niessner, Indirect Photoelectric diffusion charging of Submicron Aerosols, J.Aerosol Sci, vol. 22, No. 1, pp. 11–115 (1990).

Knutson and Whitby, Accurate Measurement of Aerosol Electric Mobility Moments, J. Aerosl. Sci., 6:453, 1975.

Knutson and Whitby, Aerosol Classification by Electric Mobility: Apparatus, Theory, and Applications, J. Aerosl. Sci., 6:443–451, 1975.

Wang, et al., Scanning electrical mobility spectrometer, Aer. Sci. Tech., 13:230, 1990.

Chi–Mun Yun et al., Development of Unipolar Ion Generator–Seperation of Ions in Axial Directio of Flow, Aerosol Science and Technology, 26:389–387 (1997).

Zhang et al., Radial differential mobility analyzer, Aer. Sci. Tech., in press, 1995.

*Primary Examiner*—Harshad Patel
*Assistant Examiner*—Robin Clark
*Attorney, Agent, or Firm*—Fish & Richardson P.C.

[57] ABSTRACT

A scanning differential mobility analysis system having a charging device, a scanning differential mobility analyzer, a flow control, and a particle detector. The charging probability and the flow rates can be dynamically adjusted according to the instant size of the particles under measurement.

13 Claims, 6 Drawing Sheets

ENHANCED AUTOMATED CLASSIFIED AEROSOL DETECTOR

This application claims the benefit of the U.S. Provisional Application No. 60/025,835, filed on Sep. 5, 1996, which is incorporated herein by reference in its entirety.

FIELD OF THE INVENTION

The present specification relates to classified particle detectors, more particularly to a scanning differential mobility analyzing system.

BACKGROUND OF THE INVENTION

Differential mobility analysis is a technique for measuring the size distribution of submicron particles i.e., particles smaller than 1.0 μm in diameter. Particles in an aerosol sample are first charged, preferably with a single electron charge, by using a charging device. The charged particles are then fed into an external electrical field between two parallel electrode plates by an accompanying gas flow. The direction of the gas flow is substantially parallel to the electrode plates. Hence, the charged aerosol particles experience two substantially perpendicular motions, one in a direction perpendicular to the electrode plates due to the force by the electrical field and another in a direction parallel to the electrode plates due to the "dragging" of the gas flow. Therefore, the particles can be classified according to their mobilities or migration velocities within discrete mobility ranges by sampling these particles after traveling a specific distance along the gas flow. This mobility classification allows for determination of the size of the classified particles if each particle is charged with only one elementary charge. Differential mobility analysis technique is known in the art. See, for example, Knutson and Whitby, in "aerosol classification by electrical mobility", J. Aerosol Sci., vol.6, p.453, 1975, which is incorporated herein by reference.

A typical differential mobility analyzer ("DMA") has a configuration of two electrodes with opposite electrical potentials. A small aerosol flow is introduced from an aerosol inlet near a first electrode and a larger particle-free sheath flow is simultaneously introduced from a sheath inlet to separate the aerosol flow from reaching a second electrode. An electrical potential drives particles of appropriate polarity across the sheath flow toward the opposite electrode. At a location downstream from the aerosol inlet, a portion of the sheath flow, which is usually small and referred to as monodisperse flow, is extracted while the remaining flow is discharged to an exhaust of the instrument ("excess flow"). Specifically, particles that migrate within a narrow range of velocities are included in the classified aerosol sample flow ("monodisperse"). Particles with higher migration velocities deposit on the second electrode while those with lower migration velocities are discharged with the exhaust flow.

Next, the classified aerosol particles are transported to a detector for counting. Any of a number of particle counting techniques may be used. For example, optical particle sizing can provide some information on relatively large particles, i.e., from 1.0 μm to as small as 0.1 or 0.05 μm in diameter. Information on the refractive index of the particulate material and the particle morphology is needed to interpret the measured data.

For submicron particles, the optical detection may be inefficient. Condensation nucleus counters (CNCs) have been developed to detect small size particles. In a CNC, small particles are grown by vapor condensation. Since a CNC can achieve high counting efficiency, rapid response, and continuous-flow, it has been widely used in combination with a DMA in an aerosol detection system.

FIG. 1 shows functional blocks of a typical aerosol detection system 100 based on differential mobility analysis. Three basic elements are shown: a charging device 110, a DMA 120, and a particle counter 130.

The particle size is inferred from the migration velocity based on the relationship between particle size and the electrical mobility of the particles. This is described by Flagan and Seinfeld in "Fundamentals of Air Pollution Engineering", Prentice-Hall, 1988. The electrical mobility, Z, is defined as the ratio of the migration velocity $v_m$ to the strength of the applied electrical field, E, $$Z = \frac{v_m}{E}. \quad (1)$$

For spherical particles carrying ν electrical charges, the mobility Z can be written as $$Z = \frac{ve}{3\Pi\mu D_p} C_c\left(2\frac{\lambda}{D_p}\right), \quad (2)$$

where μ is the gas viscosity, $D_p$ is the particle diameter, $C_c$ is an empirically-determined slip correction factor that accounts for noncontinuous aerodynamic effects, and e is the elementary unit of change. Noncontinuous aerodynamic effects may become important if the particle diameter is comparable to or smaller than the mean-free-path λ of the gas molecules. One commonly employed form for this slip correction factor $C_c$ is $$C_c = 1 + Kn\left(1.257 + 0.4\exp\left(-\frac{0.11}{Kn}\right)\right), \quad (3)$$

where $$Kn = \frac{2\lambda}{D_p} \quad (4)$$

is known as Knudsen number.

Under typical operating conditions in most practical systems, only a fraction of the particles are charged, and a majority of those charged particles carry single charge, i.e., ν=1. Most mobility classifications are performed with positively charged particles. However, negatively charged particles may also be used.

The migration velocity required for a particle to be transmitted from the aerosol inlet flow to the classified aerosol outlet flow of the differential mobility analyzers depends on the geometry of the classifier and on the four flow rates, i.e., an input sample flow rate, an input sheath flow rate, an output classified sample flow rate, and an output excess flow rate. The size of the particles to be classified is selected by adjusting the voltage such that particles with the mobility of particles of the desired size will migrate at the velocity required for transmission. The size distribution of the aerosol is determined by making measurements of the concentrations at a number of sizes spanning the size range of interest.

One critical parameter of a DMA is the size resolution, which is defined as the ratio of the mobility at which the transmission efficiency is the highest to the full width at the half value of the maximum of the DMA transfer function. A number of factors may affect the DMA resolution, including the voltage on the DMA, the diffusion of the particles as they migrate through the DMA, the particle losses to the walls of the DMA, the percentage of the particles with two or more elementary charges in the charged aerosol flow, and others.

Differential mobility analysis has traditionally been performed by making a sequence of measurements at different electric field strengths, i.e., at different voltages applied across the two electrodes of the classifier. Although this method is effective, it is usually slow. Depending on the size range and the desired resolution, the operation time may range from several minutes to more than an hour to measure a size distribution. Wang and Flagan accelerated the measurements dramatically by exponentially ramping the voltage and counting the particles continuously, thereby eliminating the delays between successive measurements that are needed to ensure representative data at each mobility with the stepping-mode of differential mobility analysis. A complete size distribution can be measured in less than one minute with this accelerated scanning-mode of differential mobility analysis. See, Wang and Flagan, "Scanning electrical mobility spectrometer" in Aerosol Sci. Technol., 13, pp.230–240, 1990.

A fully automated version of the scanning mode differential mobility analyzer system has been developed for use aboard the University of Washington C-131 during the Monterey Area Ship Track experiment. See, Russell et al., U.S. patent application Ser. No. 08/730,037, "Automated Mobility-Classified-Aerosol Detector". That instrument employed a radial differential mobility analyzer ("RDMA") in a feedback controlled system that maintained stable flows through continuous pressure variations as the aircraft altitude varied and made size distribution measurements in about 45 s. An enhanced condensation nucleus counter, produced based upon one of the commercial TSI models through collaboration with TSI, and the high transmission efficiency of the RDMA extended the sizing range of this instrument below 5 nm. The integrated system, which was termed the Radial Automated Classified Aerosol Detector (RCAD) incorporated a double bag sampler so that size distributions could be made on air drawn from discrete locations separated in flight time by only 45 s.

SUMMARY OF THE INVENTION

The present disclosure discloses an enhanced scanning differential mobility system which comprises a charging device, a scanning differential mobility analyzer, a flow control, and a particle detector.

The charging device may be a type with an adjustable charging probability that changes with the aerosol particle size under measurement. A feedback loop may be implemented to feed the size information from the scanning differential mobility analyzer back to the charging device. One embodiment of the invention uses a variable charging device with attributes of both bipolar and unipolar diffusion charging mechanisms to optimize the size range and resolution.

The flow control can dynamically adjust the rates of flows of the scanning differential mobility analyzer, including the aerosol flow, sheath flow, sample flow and the exhaust flow, in order to achieve a maximum size range and resolution for a given maximum scanning voltage.

The scanning mechanism of the charging probability and the dynamic flow control may be used independently or in combination in the scanning differential mobility system to enhance the performance.

These and other aspects and advantages of the invention will become more apparent in light of the accompanying drawings, the detailed description, and the claims.

DETAILED DESCRIPTION OF THE INVENTION

Figure 1:
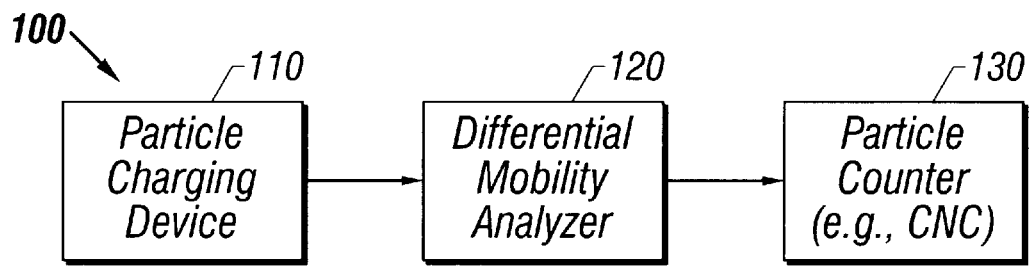
FIG. 1 is a block diagram of a classified aerosol detection system based on a differential mobility analyzer.
Figure 2:
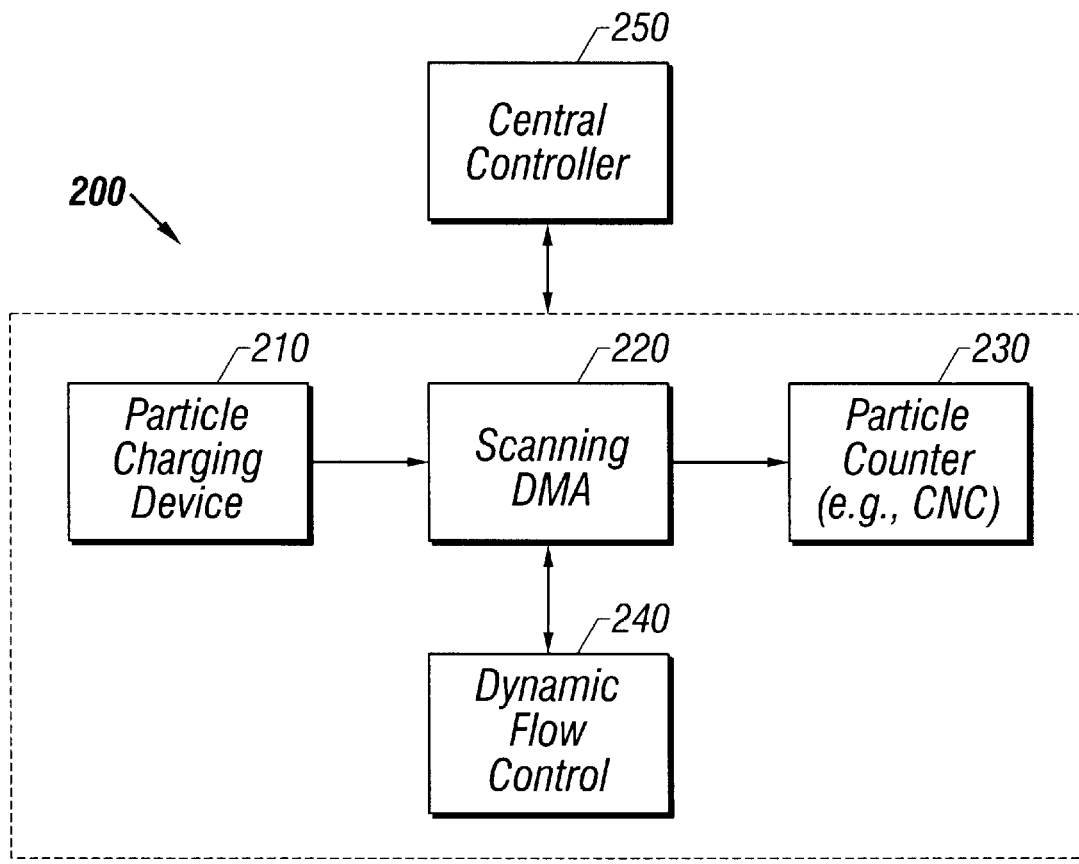
FIG. 2 is a block diagram showing one embodiment of an enhanced automated classified aerosol detection system of the invention.

FIG. 2 shows one embodiment 200 of an automated classified aerosol detection system of the invention. A particle charging device 210 receives aerosol flow samples and charges the particles therein with a certain charging probability. A scanning DMA 220, which is implemented with a voltage scanning mechanism, classifies the particles in the aerosol flow according to particle size. A particle counter 230 measures the number of particles as a function of particle size to produce a size distribution of the aerosol sample.

A dynamic flow control 240 is implemented to control the four flows in the scanning DMA 220: the aerosol flow, the sheath flow, the sample flow and the exhaust flow. One or more of the four flow rates may be dynamically scanned by the flow control 240 in order to optimize the resolution. The flow scanning may depend on the scanning voltage or the particle size.

Optionally, the embodiment 200 may include a central controller 250 to monitor and control the operations of each system component including the charging device 210 and the flow control 240. In addition, the central controller 250 may further provide a user interface.

The charging device 210 may be any charging device capable of charging the aerosol particles with either positive or negative charges. One charging mechanism suitable for the invention is based on ionization of high-energy gas molecules in a gas chamber which subsequently collide with aerosol particles and thereby produce charge on the aerosol particles. These high-energy particles collide with the aerosol particles in the chamber to remove one or more electrons from each aerosol particles. Charged aerosol particles are thus produced. The high energy particles may be produced by using a radioactive source such as Polonium.

Several types of diffusion charging devices may be used to implement the charging device 210.

One is the bipolar charger in which the gas ions produced by the collision with energetic particles are allowed to react without bias with the aerosol particles. This method produces a mixture of positively-charged and negatively charged particles with a charge distribution known as "bipolar charge distribution". Bipolar diffusion chargers are designed to charge the sample aerosol to a steady-state charge and can provide a charge distribution that is well characterized and is insensitive to operating parameters. However, the charging efficiency of bipolar chargers is dependent on the particle size. At the higher end of the size range, the bipolar charging efficiency can be high, approximately at 20% for particles at about 100 nm in diameter. At the lower end of the size range, the charging efficiency is usually low, approximately on the order of less than about 1% for particles at about 3 nm in diameter. Therefore, only a small fraction of the particles at the fine end of the size spectrum could potentially be separated by a DMA and this can drastically degrade the counting statistics.

Although charging probabilities are low for small particles, bipolar diffusion chargers do not produce significant number of particles with multiple charges if the size is below about 0.1 µm in diameter. This leads to a uniquely determined relation between particle mobility and particle size. This relation can be described by the Fuchs charge distribution which is defined in Fuchs, "On the stationary charge distribution on aerosol particles in a bipolar ionic atmosphere," Geofis. Pura Appl. Vol. 56, pp. 185–193 (1963), which is incorporated herein by reference.

Figure 3:
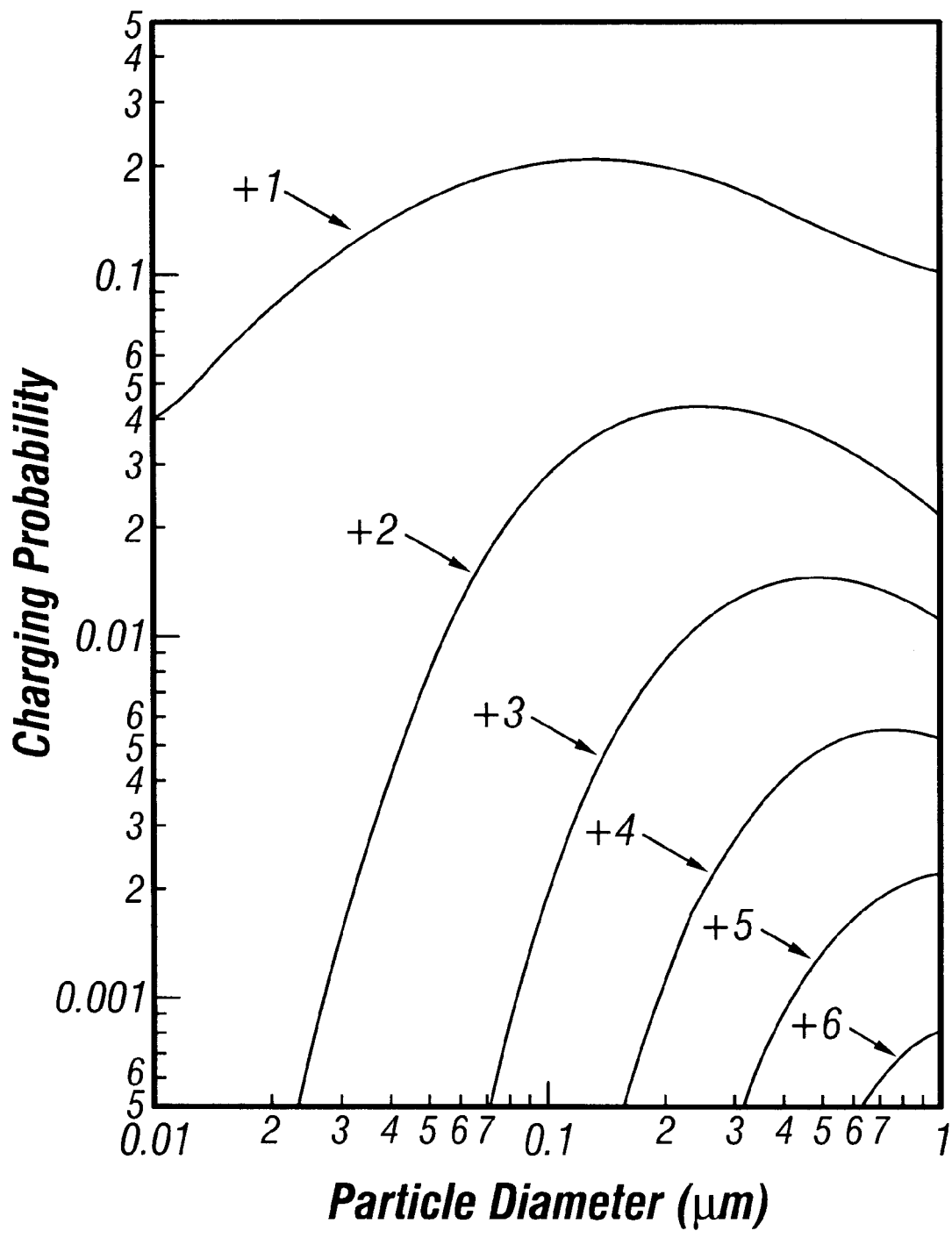
FIG. 3 is a chart showing charging probability as a function of particle size with various charges in a bipolar diffusion charger.

Wiedensohler described the bipolar charging probability $p(D_p,v)$ resulted from diffusion charging of particles by collision with ions produced by a particles in "An approximation of the bipolar charge-distribution for particles in the sub-micron size range", J. Aerosol Sci., Vol.19, pp.387–389, 1988. The results are shown in FIG. 3, which have been found to be within the experimental uncertainty of the theoretically expected value for steady-state charging of an aerosol based on the Fuchs charge distribution.

Another type of diffusion charger is the unipolar charger which contains ions with only one polarity. One method of achieving this is by using an electrical field in a chamber in which ions of both polarity are produced by collision with energetic particles generated by radioactive decay. The difference in the electrical potentials in the chamber separates the positive and negative ions that are generated through collisions with high-energy particles. This produces unipolar charged particles in the chamber. The charging efficiency of a unipolar diffusion charger is usually high at the lower end of the size spectrum in producing single-charged particles. At the higher end of the size spectrum, however, the number of the particles with multiple elementary charges increases significantly and degrades the resolution of the instrument.

One exemplary unipolar ion generator suitable for use with the invention is disclosed by Yun et al., "Development of unipolar ion generator—separation of ions in axial direction of flow," Aerosol Sco. Technol., Vol. 26, pp. 389–397 (1997), which is incorporated herein by reference. This unipolar ion generator is capable of producing concentrations of ions that are controllable and measurable. In addition, this device can charge the aerosol to much higher charging levels than what can be achieved with most bipolar diffusion chargers.

Figure 4C:
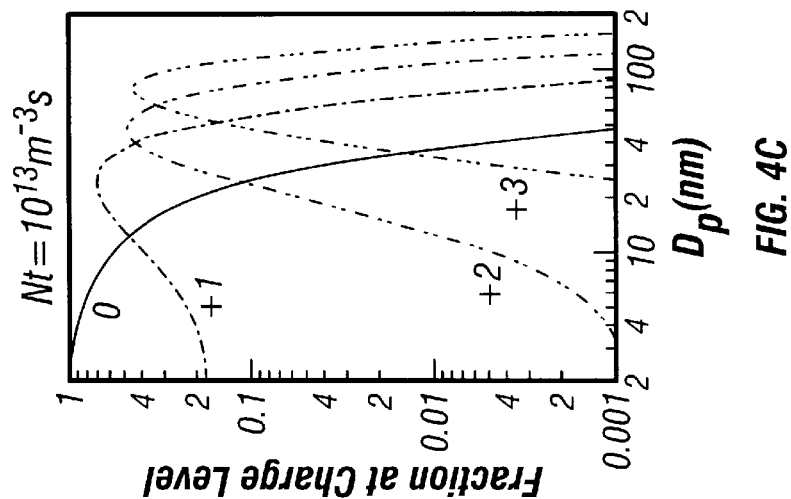
FIGS. 4B, and 4C are charts showing simulated percentage of charged particles in a unipolar diffusion charger based on Fuchs' theory under different ion densities.
Figure 4B:
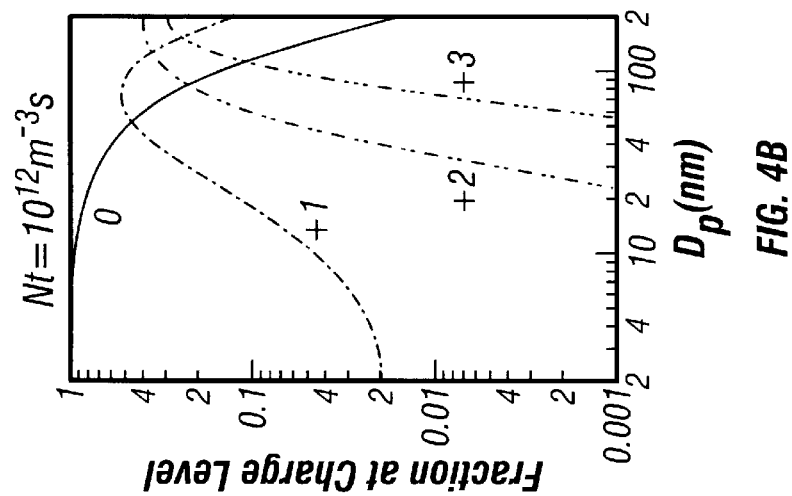
Figure 4A:
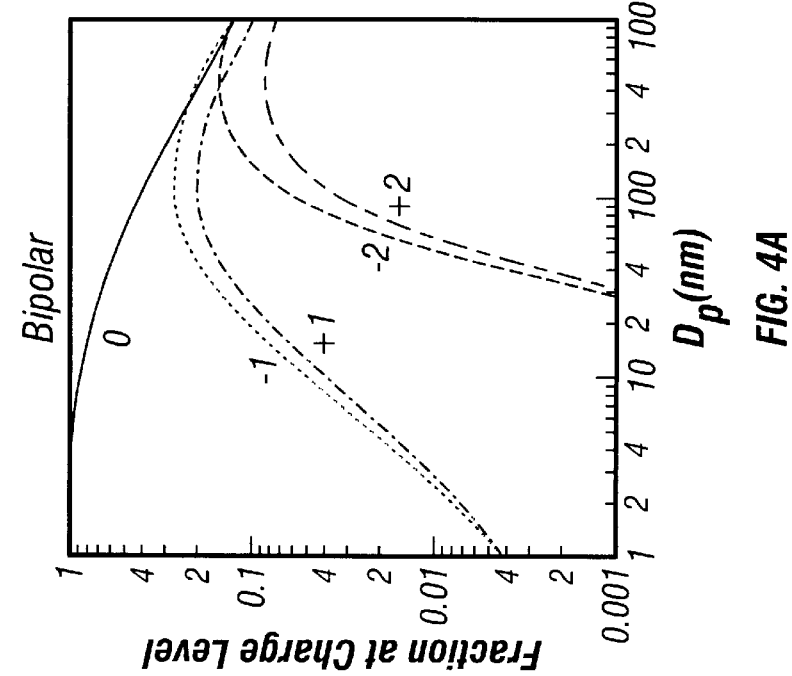
FIG. 4A is a chart showing simulated percentage of charged particles in a bipolar diffusion charger based on Fuchs' theory.

FIGS. 4A, 4B, and 4C are charts showing the diffusion charging probability as a function of particle size based on Fuchs charge distribution. FIG. 4A shows the results for bipolar diffusion charging. The charging probability for single elementary charge (positive or negative) drops significantly (about 4%) when the particle size is below about 10 nm. Multiple charging is insignificant for sizes smaller than about 50 nm. For particles greater than about 150 nm, the fraction of the particles with multiple charges becomes appreciable.

FIGS. 4B and 4C show charging probabilities for unipolar diffusion charging under two different ion concentration ($N_i$)-residence time (t) products. In FIG. 4B, $N_i t=10^{12} m^{-3} s$ and in FIG. 4C, $N_i t=10^{13} m^{-3} s$. Clearly, the particles charged with multiple elementary charges become problematic when the particle size increases to above 40 nm in unipolar charging. FIG. 4C further indicates that a high charging efficiency can be achieved for particles of several nanometers. For example, the efficiency is nearly 20% at about 2 nm.

The inventors recognized the limitations of bipolar and unipolar diffusion charging techniques and their effects on the resolution and further recognized that these limitations may be alleviated by a charging device which can dynamically adjust the charging probability with the size of the particles under measurement. The exact charging probability may be controlled according to a relationship with the particle size. In particular, the charging probability at small particle sizes may be enhanced to optimize the counting statistics by enhancing the proportion of the singly charged particles and the resolution by minimizing the proportion of the particles with two or more elementary charges.

A charging device 210 according to this aspect of the invention should be able to produce a variable charging probability that can be adjusted continuously and rapidly with the particle size. In operation, when measuring particles smaller than about 40 nm in diameter, the variable charging device is configured to have a high charging probability in order to improve the counting statistics by charging a large fraction of the aerosol particles. For particles larger than about 100 nm, however, the variable charging device is configured to have a low charging probability to minimize the fraction of particles carrying multiple charges. Thus, the charging probability of the charging device and the mobility size range of the DMA are synchronized with respect to each other.

Figure 5:
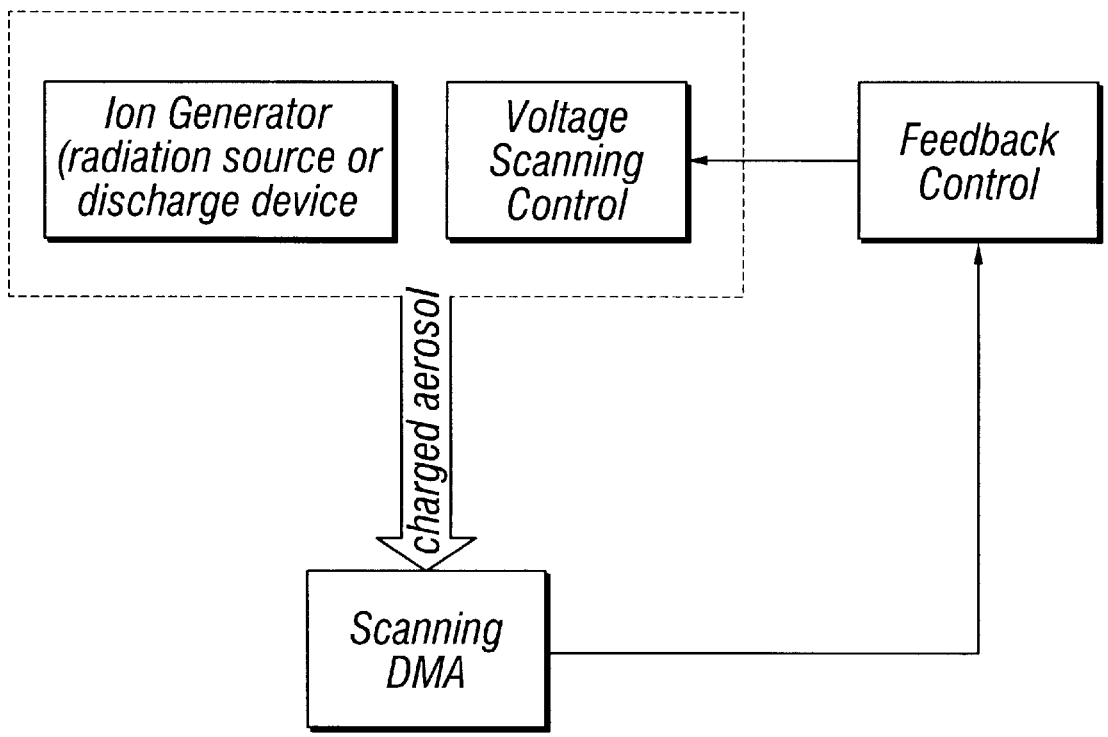
FIG. 5 is a block diagram showing a diffusion charging device with a voltage scanning control and feedback circuit.

One embodiment of this aspect of the invention is essentially a variable diffusion charger that has attributes of both unipolar and bipolar diffusion chargers. A voltage-scanning mechanism is implemented to change the potential difference in the charging chamber. A feedback circuit is connected between the DMA control circuit and the voltage-scanning mechanism so that the voltage applied to the charging chamber is automatically adjusted with the mobility range that is fed from the DMA control circuit. FIG. 5 shows a functional block diagram of this variable diffusion charger.

In operation, when the DMA is set to measure particles at the low end of the size spectrum, the voltage on the charging chamber is adjusted accordingly to the high values so that the charger functions as a unipolar charger. This way, the fraction of the fine particles charged with an elementary charge is maximized. As the DMA measures particles in the medium size range, the voltage on the charging chamber also decreases to optimize the charging probability for producing singly charged particles. When the DMA approaches the high end of the size spectrum, the voltage on the charging chamber is set to a minimum value (or even zero) so that the charger is effectively a bipolar charger.

The ion concentrations may be adjusted according to the particle size under measurement to mitigate the multiple charging problem. This technique is illustrated by FIGS. 4B and 4C. For example, if the ion density-residence time product is $N_it=10^{13} m^{-3}s$ as shown in FIG. 4C, the size at which the numbers of singly and doubly charged particles become equal is about 40 nm. Thus, reliable classification measurements can be achieved for particles smaller than 40 nm under $N_it=10^{13} m^{-3}s$. For particles at 40 nm or larger, the number of particles with two or more elementary charges becomes significant and there is no longer a unique relation between the mobility and particle size. This problem may be alleviated by changing the ion density-residence time product $N_it$. Specifically, Nit in the charger may be decreased as the DMA is set to measure larger particles. For example, if the ion density-residence time product Nit is reduced from $10^{13} m^{-3}s$ to $10^{12} m^{-3}s$, the size at which the numbers of singly and doubly charged particles become equal is shifted from 40 nm to about 80 nm (FIG. 4C). Further reductions in the ion density can increase the double charging threshold to even larger sizes.

In addition to the use of high-energy particle emission of a radio-active source, other charging techniques may also be used in practicing the invention. Corona discharge, for example, may be used to generate ions in the charging chamber. The discharge region can be electrically isolated from the area through the aerosol particles flow. The isolation can be accomplished by using a grid in the charging chamber. The generated ions from the corona discharge are injected into the aerosol flow through the grid at a rate based on an imposed electrical field. This provides a controllable ionization so that the charging probability can be dynamically adjusted with the particle size under measurement. In addition, corona discharge eliminates the need for using radioisotopes sources which can be inconvenient in some applications.

Photoemission from a metallic surface is another ion production technique for diffusion charging. Two implementations of this technique are disclosed by Bucholske and Niessner in "Indirect photoelectric diffusion charging of submicron aerosols", J. Aerosol Sco., Vol. 22, pp. 111–115 (1991) and Seto et al. in "Fine particulate contaminant control by the UV phoelectro method under a low pressure condition", Review of Scientific Instruments, Vol. 66, pp. 5348–5350 (1995), which are incorporated herein by reference.

Another aspect of the invention is an implementation of a flow scanning mechanism to control the flow rates at the scanning DMA 220 in the embodiment 200 (FIG. 2). This may be accomplished by a dynamic flow control 240. The flow scanning mechanism can be used to extend the analytical size range and the detection sensitivity.

The range of particle size range of a differential mobility analyzer is at least in part limited by the range of voltages over which the DMA can safely be operated. At potentials exceeding about 10 KV, arcing within the DMA may become a problem which can create both flight safety hazards and the risk of damage to the delicate classification region of the DMA. In addition, precision control of the DMA over wide voltage ranges can be difficult. This is because of the limited resolution of digital-to-analog converters and the difficulty of producing a high voltage power supply with a wide dynamic range (e.g., covering four decades). Moreover, the resolution of the DMA decreases at the lower end of the size spectrum due to diffusion of the particles as they migrate through the DMA.

The dependence of the measurable size range on the voltage may be understood by comparing the transport migration to the diffusion migration by using the migration Peclet number:

$$P_e = \frac{v_{mig} b}{D} = \frac{EZb}{D}, \tag{5}$$

where $v_{mig}$ is the migration speed, b the gap between the electrodes, and D the particle diffusivity, E the electrical field, and Z the particle mobility. Since $Z vD/kT$, where v is the charge on the particle, k is Boltzmann constant, and T is the temperature, the Peclet number $P_e$ can be written as:

$$P_e = \frac{vV}{kT}. \tag{6}$$

The diffusion effect is represented by the thermal energy kT and the transport due to the electrical field is represented by electrical energy vV. Equation (6) indicates that the operating voltage of the DMA is a primary operating parameter that determines the relative importance of diffusion for a given DMA. In general, the higher the voltage, the higher the resolution. But the upper bound of the DMA voltage is essentially limited by the electrical breakdown. Theoretically, there is no physical limit to the lower bound of the DMA voltage. However, in a practical implementation, a lower bound of the DMA voltage is limited by the diffusional broadening of the DMA transfer function which determines the DMA resolution.

Figure 6:
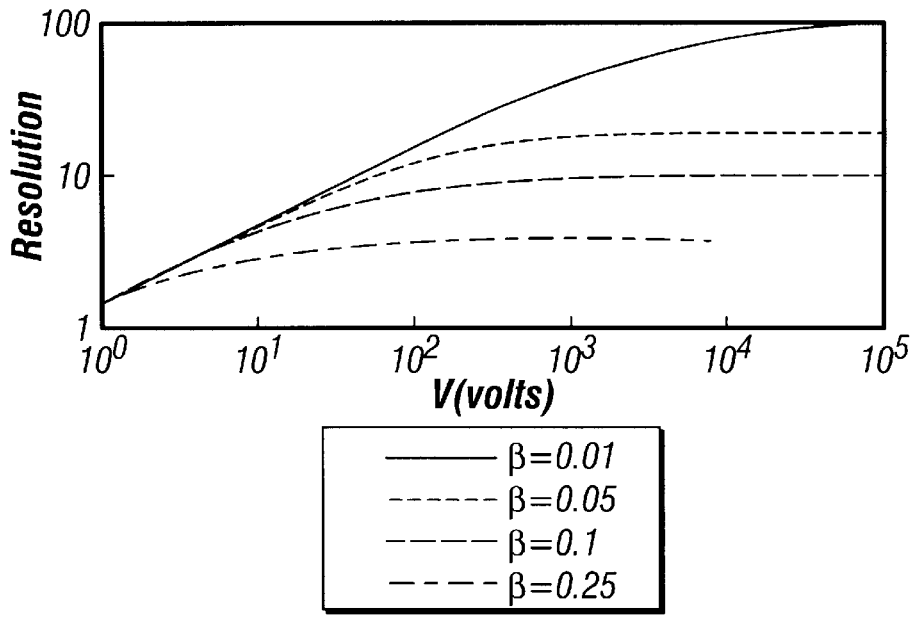
FIG. 6 is a chart showing the DMA resolution as a function of the DMA voltage under various flow conditions.

FIG. 6 shows the DMA resolution as a function of the DMA voltage under various flow conditions. A flow parameter $\beta$ is defined as the ratio of the sum of the aerosol and monodisperse flows to the sum of the sheath and excess flows:

$$\beta = \frac{Q_{aerosol} + Q_{monodisperse}}{Q_{sheath} + Q_{exhaust}}. \tag{7}$$

It should be noted that the asymptotic resolution of the DMA at high voltages is inversely proportional to flow parameter $\beta$.

For $\beta=0.1$, the voltage as low as 100V may be used without serious degradation of the DMA resolution, but the resolution decreases rapidly as the potential is below that point. Since the voltage range for high resolution operation is limited to about two decades, and for the small particles the mobility scales inversely with the square of the particle diameter, only about a decade in diameter can be covered without degraded resolution. For larger particles, the mobility approaches the continuum limit for which Z is inversely proportional to the diameter and perhaps two decades can be analyzed with good resolution.

The inventors achieved a measurable range from about 3 nm to 150 nm diameter with a DMA voltage scanning range from about 9000 V to a few volts. Such operation scheme sacrifices the resolution at the low end of the size spectrum. However, the size range can be further extended to cover both the ultra fine aerosol and the larger optically active particles.

A preferred approach to extend the size range of the DMA is to simultaneously scan the flows of the DMA in synchronization with the scan of the DMA voltage. Preferably, the flow rate scan is in the opposite direction of the DMA voltage scan. Therefore, as the DMA scans through the size spectrum from small particles to large particles, each flow rate is adjusted to change from a minimum rate to a maximum value. The flow rate scanning can increase the size range and improve the counting statistics for the fine particles.

Any scanning DMA may be used to implement the present invention. The following description will use the radial DMA as an example to illustrate the flow rate scanning. For a RDMA, the centroid mobility, Z*, is $$Z^* = \frac{(Q_{sh} + Q_e)b}{2\pi(R_2^2 - R_1^2)V}, \quad (8)$$

where $R_1$ is the radius of the sample outlet for the sample flow, $R_2$ is the position of the aerosol inlet relative to the center of the sample outlet, $Q_{sh}$ the sheath flow rate, and $Q_e$ the excess flow rate. The volumetric flow rate, Q, is related to the instantaneous RDMA voltage, V, by $$Q = Q_{min} \exp\left(\frac{\ln\frac{Q_{max}}{Q_{min}}}{\ln\frac{V_{max}}{V_{min}}} \ln\frac{V}{V_{min}}\right), \quad (9)$$

where $V_{min}$ is a predetermined minimum RDMA voltage, $Q_{man}$ and $Q_{min}$ are the maximum and minimum rates.

An exponential ramp (up or down) in the mobility of the transmitted particles is preferred. This can be accomplished by exponentially scanning both the voltage and flow rates in opposite directions. Given a target minimum size to be detected (maximum mobility), maximum applied voltage, and allowable range of flow rates (which is determined by flow stability issues), the optimal operating trajectory for the DMA can readily be determined.

Figure 7:
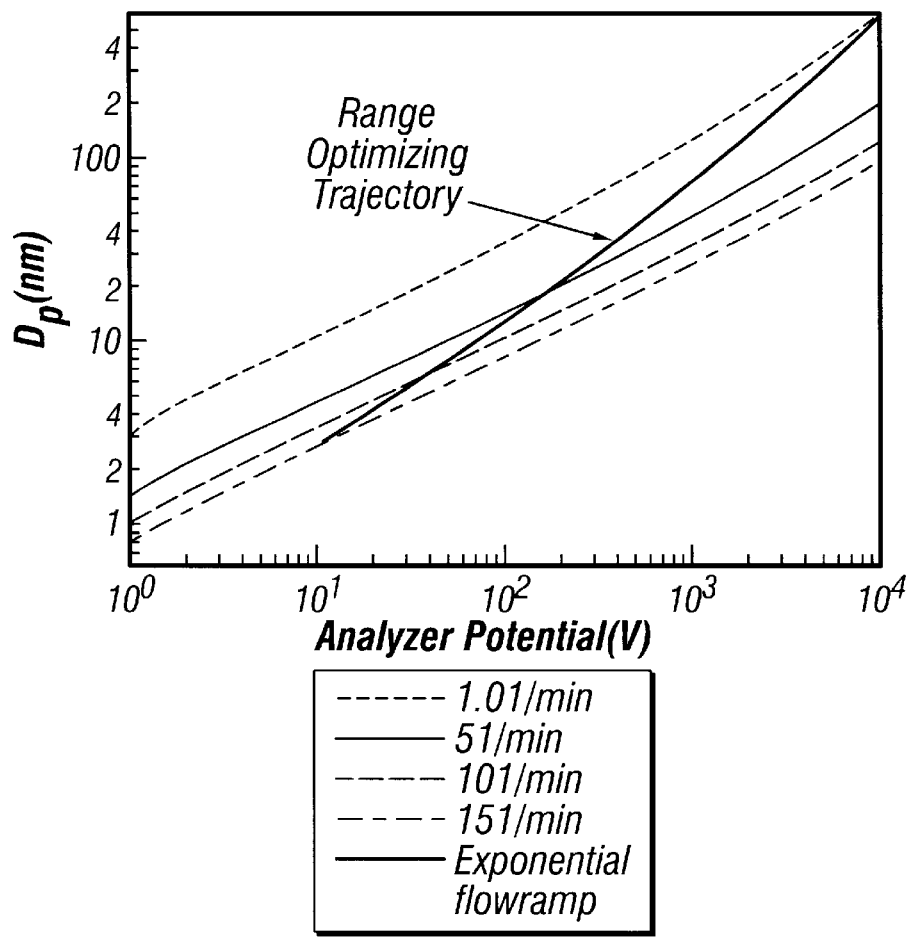
FIG. 7 is a chart showing measured variation of the centroid particle size as a function of RDMA under different flow rates.

FIG. 7 shows the measured variation of the centroid particle size as a function of RDMA voltage for different flow rates. The flow rate and voltage scan undergo exponential ramps. At the minimum particle size, the applied voltage as shown is at a very low value, only about 12 V, so diffusion broadening of the DMA transfer function is substantial. The measurements at a fixed sheath flow rate of $Q_{Sh}$=5 l/min produced substantially greater broadening than achieved when the fine particle measurements are made at a higher flow rate. At the same time the maximum size transmitted is increased to 600 nm rather than 180 nm that was achieved with a fixed flow rate.

The exponential scan of the flow rates is only an example. More complex scanning trajectories may be used in scanning the flow rate and the DMA voltage to improve the resolution. In operation, the dynamic range may be maximized by executing the following steps. First, the DMA voltage is increased as rapidly as possible while holding the flow rate constant at the maximum value. Second, the flow rate is reduced when necessary to extend the range and a constant mobility ramp time is maintained throughout the dual ramp.

Figure 8:
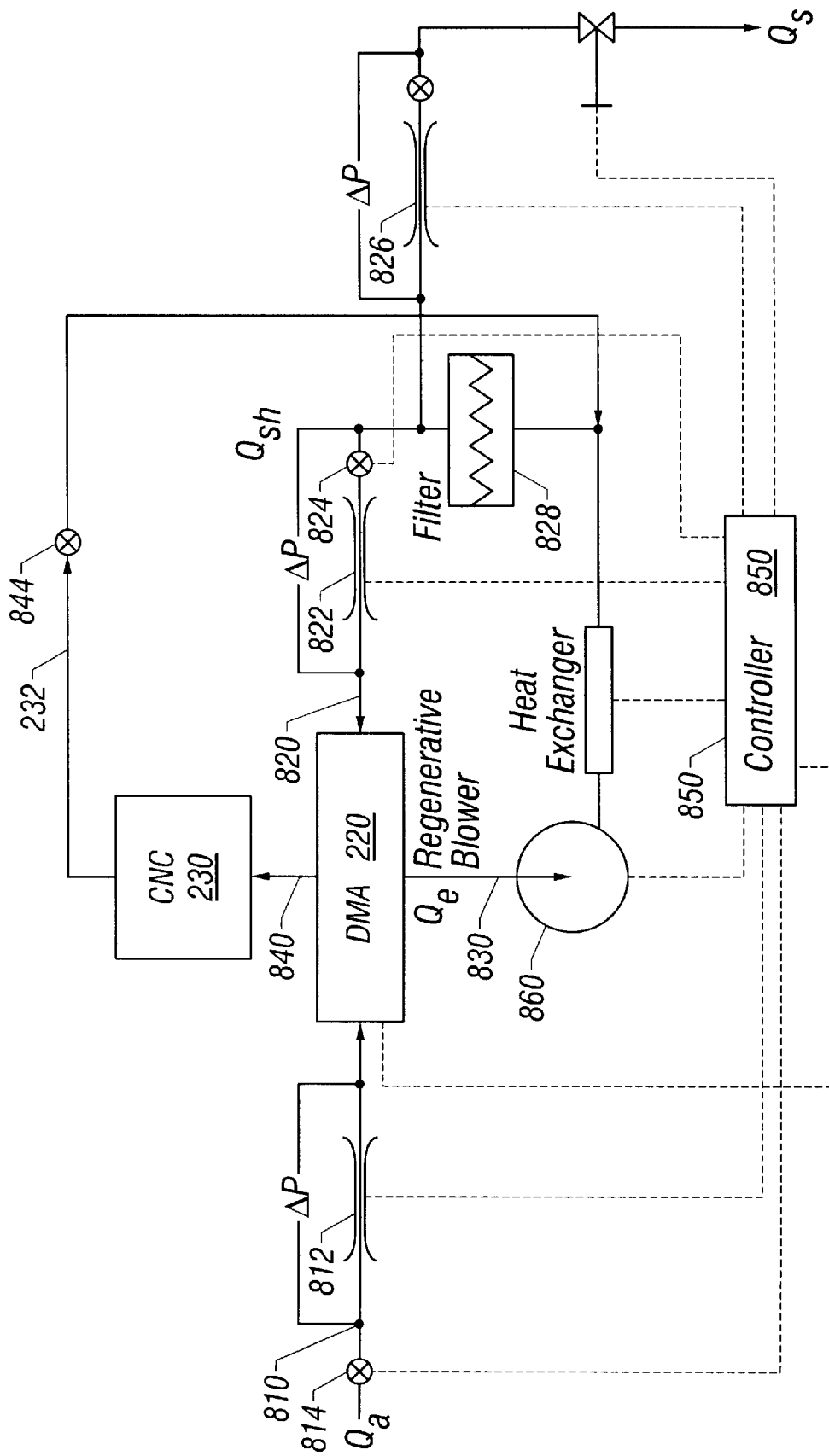
FIG. 8 is a block diagram showing one embodiment of the dynamic flow control in accordance with the invention.

FIG. 8 illustrates one embodiment of the dynamic flow control scheme and the associated flow paths for the dynamic flow control 240 of FIG. 2. The solid lines represent the flow paths and the dashed lines represent the electrical paths. The DMA 220 receives two input flows, an aerosol flow 810 and a sheath flow 820. Flow control valves 814 and 824 regulate the flow rates of the aerosol flow 810 and the sheath flow 820, respectively. The flow rates $Q_a$ and $Q_{sh}$ are measured by flow elements 812 and 822, which may be, for example, a laminar flow element. A controller 850 is implemented to monitor and control the flow rates by communicating with the flow valves and flow elements. The controller 850 also controls the operation of the scanning DMA 220.

The sheath flow 820 may be generated from an external source such as from the input aerosol flow or from recirculation of the excess flow 830. The output flow 232 from the CNC 230 may also be recirculated to the sheath flow 820 as shown in FIG. 8. A regenerative variable speed regenerative blower 860 may be used to recirculate the sheath air and reduces the number of flow control valves required to one at the outlet of the CNC 232.

An adaptive control of the DMA ramp voltage may also be implemented. A further safeguard is a voltage anomaly detector that monitors the DMA voltage and automatically reduces the voltage if evidence of an arc is detected.

Although the present invention has been described in detail with reference to the preferred embodiment, one ordinarily skilled in the art to which this invention pertains will appreciate that various modifications and enhancements may be made without departing from the spirit and scope of the following claims.

What is claimed is:

1. A differential mobility analyzing system, comprising:
   a controllable charging device, receiving a gaseous flow and transferring electrical charge to particles in the gaseous flow, operable to generate an ion density that progressively changes with time during measurement so as to produce a single elementary charge on particles of different sizes within a size range;
   a scanning differential mobility analyzer coupled to said controllable charging device to receive the gaseous flow from said controllable charging devices and operable to classify the particles according to particle mobility in response to a scanning control voltage;
   a flow control module coupled to continuously change at least a flow rate of the gaseous flow from said controllable charging device into said scanning differential mobility analyzer in time during measurement so that the flow rate continuously chances with an instantaneous value of said scanning control voltage to increase the resolution and dynamic range of said scanning differential mobility analyzer;
   a feedback circuit electrically interconnecting said controllable charging device and said scanning differential mobility analyzer operating to continuously adjust a charging probability of said controllable charging device in time during measurement by controlling the ion density in a relation with said scanning control voltage to substantially increase a number of particles that are charged with a single elementary charge within a range of voltage values of said scanning control voltage; and
   a particle counter connected to said scanning differential mobility analyzer to receive the classified particles and configured to measure the number of the classified particles.

2. A system as in claim 1, wherein said flow control module operates to change the magnitude of said flow rate in an opposite direction to said scanning control voltage.

3. A system as in claim 1, wherein said flow rate of the gaseous flow and said scanning control voltage each change according to an exponential function.

4. A system as in claim 1, wherein said controllable charging device is a variable diffusion charging device having a voltage scanning mechanism that changes a potential difference of a charging chamber.

5. A system as in claim 1, wherein said controllable charging device includes a charging chamber that produces charge on particles by corona discharge.

6. A differential mobility analyzing system, comprising:
   a charging device operable to produce a time-varying ion density to transfer a single elementary charge to particles in an aerosol flow of particles of different sizes within a size range;

a scanning differential mobility analyzer having an aerosol input port coupled to receive said aerosol flow, a sheath input port that receives a sheath flow, a sample output port for exporting a classified aerosol sample flow generated from said aerosol flow, and an exhaust output port for exporting a exhaust flow, said scanning differential mobility analyzer classifying the particles in said aerosol flow according to particle mobility in response to a scanning control voltage;

a flow control module communicating with said scanning differential mobility analyzer to continuously and simultaneously adjust each flow rate of said aerosol flow, said sheath flow, said classified aerosol sample flow, and said exhaust flow to vary in time during measurement according to an instantaneous value of said scanning control voltage to increase the resolution and dynamic range of said scanning differential mobility analyzer;

a feedback circuit electrically interconnecting said charging device and said scanning differential mobility analyzer and operating to adjust the charging probability of said charging device in a relation with said scanning control voltage during measurement to substantially increase a number of particles that are charged with a single elementary charge within a range of voltage values of said scanning control voltage; and a particle counter connected to said scanning differential mobility analyzer to receive said classified aerosol sample flow and configured to measure the number of the classified particles.

7. A system as in claim 6, wherein said flow control module operates to change the magnitude of said each flow rate in the opposite direction to said scanning control voltage.

8. A system as in claim 6, wherein said controllable charging device is a variable diffusion charging device having a voltage scanning mechanism that changes a potential difference of a charging chamber.

9. A system as in claim 6, wherein said controllable charging device includes a charging chamber that produces charge on particles by corona discharge.

10. A system as in claim 6, further comprising a flow path connected to receive said exhaust flow and operable to process and recirculate said exhaust flow to produce said sheath flow to said sheath input port.

11. A method for measuring a size distribution of particles in a gaseous flow by using a differential mobility analyzer, comprising:

receiving a gaseous flow and transferring electrical charge to particles in the gaseous flow in a charging chamber;

controlling a charging probability of the charging chamber to produce a time-varying ion density;

using a differential mobility analyzer to receive the gaseous flow from the charging chamber and to classify the particles according to particle mobility in response to a scanning control voltage;

continuously adjusting at least a flow rate of the aerosol flow into the scanning differential mobility analyzer to produce a time-varying flow rate in response to an instantaneous value of said scanning control voltage to increase resolution and dynamic range of the scanning differential mobility analyzer;

continuously adjusting the charging probability in a relation with said scanning control voltage to substantially increase a number of particles that are charged with a single elementary charge within a range of voltage values of said scanning control voltage; and measuring the number of the particles that are classified by the differential mobility analyzer.

12. A method as in claim 11, wherein said flow control module operates to change the magnitude of said each flow rate in the opposite direction to said scanning control voltage.

13. A method as in claim 11, wherein the scanning differential mobility analyzer has an aerosol input port coupled to receive said aerosol flow, a sheath input port that receives a sheath flow, a sample output port for exporting a classified aerosol sample flow generated from said aerosol flow, and an exhaust output port for exporting a exhaust flow, and further comprising simultaneously changing flow rates of said flows in a way that each flow rate changes its magnitude in an opposite direction to the scanning control voltage.

* * * * *